United States Patent
Kong et al.

(10) Patent No.: US 11,124,826 B2
(45) Date of Patent: Sep. 21, 2021

(54) KITS COMPRISING NUCLEIC ACID TEMPLATES AND PRIMERS FOR USE IN PRE-AMPLIFICATION ASSAYS

(71) Applicant: Bio-Rad Laboratories, Inc., Hercules, CA (US)

(72) Inventors: Yanhong Kong, Hercules, CA (US); Steven Okino, San Carlos, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 305 days.

(21) Appl. No.: 16/108,612

(22) Filed: Aug. 22, 2018

(65) Prior Publication Data

US 2019/0078135 A1    Mar. 14, 2019

Related U.S. Application Data

(62) Division of application No. 14/702,433, filed on May 1, 2015, now Pat. No. 10,077,469.

(60) Provisional application No. 61/987,921, filed on May 2, 2014.

(51) Int. Cl.
*C12Q 1/6876* (2018.01)
*C12Q 1/686* (2018.01)
*C12Q 1/6853* (2018.01)

(52) U.S. Cl.
CPC .......... *C12Q 1/686* (2013.01); *C12Q 1/6853* (2013.01); *C12Q 1/6876* (2013.01); *C12Q 2527/143* (2013.01); *C12Q 2527/146* (2013.01); *C12Q 2545/101* (2013.01)

(58) Field of Classification Search
CPC .... C12Q 1/686; C12Q 1/6876; C12Q 1/6853; C12Q 2527/146; C12Q 2527/143; C12Q 2545/101
See application file for complete search history.

(56) References Cited

U.S. PATENT DOCUMENTS

| | | | |
|---|---|---|---|
| 5,925,733 A * | 7/1999 | Rose | C12N 9/1252 530/350 |
| 7,531,328 B2 | 5/2009 | Gerdes et al. | |
| 8,304,214 B2 | 11/2012 | Gerdes et al. | |
| 8,323,897 B2 | 12/2012 | Andersen et al. | |
| 2005/0239116 A1 | 10/2005 | Willey | |
| 2007/0092869 A1 | 4/2007 | Fulmer-Smentek et al. | |
| 2009/0011053 A1* | 1/2009 | Cho | A61K 36/258 424/728 |
| 2012/0190010 A1 | 7/2012 | Eickhoff et al. | |

FOREIGN PATENT DOCUMENTS

| | | |
|---|---|---|
| CN | 101821619 A | 9/2010 |
| WO | 2012171997 A1 | 12/2012 |
| WO | 2013177265 A1 | 11/2013 |

OTHER PUBLICATIONS

Zimmermann et al. BioTechniques 1997; 23: 882-888 (Year: 1997).*
International Search Report and Written Opinion from PCT/US2015/028845, dated Aug. 5, 2015.
(Continued)

*Primary Examiner* — Angela M. Bertagna
(74) *Attorney, Agent, or Firm* — Kilpatrick Townsend and Stockton LLP

(57) ABSTRACT

Provided herein are methods and compositions to determine the efficacy of a nucleic acid pre-amplification reaction.

16 Claims, 9 Drawing Sheets

(56) References Cited

OTHER PUBLICATIONS

Exiquon. "miRCURY LNA Universal RT microRNA PCR, RNA Spike-In Kit." Product manual. Jun. 2013 [retrieved on Jul. 21, 2015]. Retrieved from the Internet at : exigon.com/ls/Documents/Scientific/PCR-spike-in-manual.pdf.

Black et al., "Determining Fungi rRNA Copy No. by PCR," 2013, *J. Biomol. Tech.*, 24(1):32-38.

Derveaux, S., How to Do Successful Gene Expression Analysis Using Real-Time PCR, 2010, *Methods*, 50(4):227-230.

Roberts et al., "Assessment of RT-qPCR Normalization Strategies for Accurate Quantification of Extracellular microRNAs in Murine Serum," Feb. 2014., *PLoS One* 9(2):e89237, 14 pages.

Tan et al., "Evaluation of Extraction Kits and RT-qPCR Systems Adapted to High-Throughput Platform for Circulating miRNAs," Mar. 24, 2015, *Scientific Reports*, vol. 5, Article 9430; pp. 1-8.

European Application No. EP15786827.4 "Extended European Search Report", dated Oct. 28, 2016, 9 pages.

Karatayli, et al., "A one step real time PCR method for the quantification of hepatitis delta virus RNA using an external armored RNA standard and intrinsic internal control", *Journal of Clinical Virology* vol. 60, Issue 1, 2014, pp. 11-15.

Troxler, et al., "TagMan Real-Time Reverse Transcription-PCR Assay for Universal Detection and Quantification of Avian Hepatitis E Virus from Clinical Samples in the Presence of a Heterologous Internal Control RNA", *Journal of Clinical Microbiology*, American Society for Microbiology, vol. 49, No. 4, Apr. 2011, pp. 1339-1346.

Mengual et al.; "Multiplex preamplification of specific cDNA targets prior to gene expression analysis by TaqMan Arrays"; *BMC Research Notes*; vol. 1, No. 21; Jun. 5, 2008; 8 pages.

* cited by examiner

PASIC assay components

The PASIC assay

C1 and C2 may be on the same strand and have a non-overlapping template

C1 and C2 may be on the same strand and have an overlapping template

KITS COMPRISING NUCLEIC ACID TEMPLATES AND PRIMERS FOR USE IN PRE-AMPLIFICATION ASSAYS

CROSS-REFERENCE TO RELATED PATENT APPLICATIONS

This application is a divisional of U.S. patent application Ser. No. 14/702,433 filed May 1, 2015, now U.S. Pat. No. 10,077,469, issued Sep. 18, 2018, which claims benefit of priority to U.S. Provisional Patent Application No. 61/987,921, filed, May 2, 2014, each of which is incorporated by reference for all purposes.

BACKGROUND OF THE INVENTION

Analysis of nucleic acids often requires amplification of a sequence or set of sequences prior to the more detailed downstream analysis. This can be because the sequences under investigation are rare in a sample, or because the downstream analysis requires a large amount of starting material. Samples obtained from biological sources or the environment can, however, include factors that inhibit amplification. In addition, there is variability between samples. For example, a blood sample from one individual may include more inhibitory factors than a blood sample from another, such that the pre-amplification step is less effective in the first sample. These issues can make downstream analysis more difficult or lead to inconsistent results between samples.

BRIEF SUMMARY OF THE INVENTION

Provided herein are methods and components that can be used to establish the efficacy of an amplification reaction. Such components can be added to a sample assay and act as an internal control for the amplification reaction.

Provided herein are methods for detecting a condition (e.g., less-than-expected amplification due to an abnormality or inhibitor) in a first nucleic acid amplification reaction, the methods comprising:

assembling a first mixture, wherein the first mixture comprises a first nucleic acid template (e.g., a single- or double-stranded nucleic acid), a second nucleic acid template, and a first set of primers specific for the first nucleic acid template (e.g., capable of hybridizing to the first nucleic acid template);

carrying out the first amplification reaction with the first mixture for a first number of cycles to generate a product (e.g., including an amplification product of the first nucleic acid template);

assembling a second mixture, wherein the second mixture comprises the product (e.g., an aliquot or diluted aliquot of the product), a second set of primers specific for the second nucleic acid template, and a third set of primers specific for an amplification product of the first nucleic acid template;

carrying out a second amplification reaction with the second mixture;

determining and comparing the number of cycles required to reach Cq for amplification of the first nucleic acid template (Cq1) and the number of cycles required to reach Cq for amplification of the second template (Cq2); and detecting a condition in the first amplification reaction when the difference between the number of cycles required to reach Cq2 and the number of cycles required to reach Cq1 (ΔCq) is less (e.g., 2%, 5%, 10%, 20%, 30%, 40%, 1-20%, or 5-30% less) than a threshold number of cycles (e.g., the first number of cycles when the amount of the first nucleic acid template and second nucleic acid template are present in the same amount in the first mixture).

In some embodiments, the first nucleic acid template and second nucleic acid template are on separate nucleic acid molecules. In some embodiments, the first nucleic acid template and second nucleic acid template are non-overlapping templates on a single nucleic acid molecule. See, e.g., FIG. 1C. In some embodiments, the first nucleic acid template and second nucleic acid template are overlapping templates on a single nucleic acid molecule. See, e.g., FIG. 1D.

In some embodiments, the first mixture further comprises a sample (e.g., a biological sample, or other sample suspected of including a nucleic acid of interest). In some embodiments, the first mixture further comprises a fourth set of primers specific for a sample nucleic acid template (e.g., a template included on the suspected nucleic acid of interest). In some embodiments, the sample nucleic acid template includes a genetic variant (e.g., CNV, SNP or mutation). In some embodiments, the second mixture further comprises a fifth set of primers specific for a sample nucleic acid template. In some embodiments, the fourth and fifth sets of primers are the same. In some embodiments, the fourth and fifth sets of primers are different (e.g., complementary to different or overlapping sequences on the sample nucleic acid template, or differently labeled).

In some embodiments, the first amplification reaction is multiplex, e.g., designed to amplify multiple sample nucleic acid templates. In some embodiments, the first mixture thus further includes multiple sets of primers specific for multiple sample nucleic acid templates. In some embodiments, the second amplification reaction is multiplex. In some embodiments, the second mixture further includes multiple sets of primers specific for the amplification products of sample nucleic acid templates from the first amplification reaction. In some embodiments, the product of the first amplification is split between multiple "second" mixtures, each designed to detect one or more distinct amplification products of sample nucleic acid templates from the first amplification reaction.

In some embodiments, the first nucleic acid template and second nucleic acid template are present in equal amounts in the first mixture. In some embodiments, the first nucleic acid template and second nucleic acid template are on the same nucleic acid molecule (single- or double-stranded). In some embodiments, the first and second nucleic acid templates are the same length or within 1-50 nucleotides of being the same length. In some embodiments, the first and second nucleic acid templates are 50-2000 nucleotides in length, e.g., 80-120 or 100-500 nucleotides, or about 100, 200, 250, 300, 500, or 750 nucleotides in length.

In some embodiments, the first set of primers is the same as the third set of primers. In some embodiments, the first and third sets of primers are different (e.g., complementary to different or overlapping sequences on the first nucleic acid template, or differently labeled).

In some embodiments, the first amplification reaction is PCR. In some embodiments, the first number of cycles is between 1 and 25 (e.g., 4-10, 5-15, 2-8, 6-20, 10-24, etc.). In some embodiments, a condition (e.g., abnormality or inhibition) is detected when the difference between the number of cycles required to reach Cq2 and the number of cycles required to reach Cq1 is about 0.01-5 cycles (e.g., 0.1-1, less than 1, 0.01-2, 3, 4, 5, 2-5) less than the threshold number of cycles. In some embodiments, the first amplification reaction is reverse transcription. In some embodiments, the first nucleic acid template is RNA and the second nucleic acid template is DNA. In some embodiments, a condition (e.g., abnormality or inhibition) is detected when the difference between the number of cycles required to reach Cq2 and the number of cycles required to reach Cq1 is 0.01-2, (e.g., where the amount of first and second nucleic acid templates is equal (or as close as possible)). In some embodiments, the second amplification reaction is PCR, e.g., qPCR (real time PCR or digital PCR). In some embodiments, the second amplification reaction is carried out for a second number of cycles. In some embodiments, the second number of cycles is equal to or greater than the first number of cycles.

In some embodiments, the first set of primers is at least partially removed from the product before assembling the second mixture. In some embodiments, the product is diluted at least 2-fold (e.g., 5-fold, 10-fold, 20-fold, 10- to 100-fold) in the second mixture, e.g., as a result of aliquotting.

Further provided are methods for detecting a condition (e.g., less than expected amplification) in a first amplification reaction, the methods comprising:
assembling a first mixture, wherein the first mixture comprises a first nucleic acid template, a second nucleic acid template, and a first set of primers specific for the first nucleic acid template;
carrying out the first amplification reaction with the first mixture for a first number of cycles to generate a product;
assembling a second mixture, wherein the second mixture comprises the product, and reagents for carrying out a second nucleic acid assay;
carrying out the second nucleic acid assay with the second mixture;
determining a signal indicative of the amount of first nucleic acid template in the second mixture and a signal indicative of the amount of second nucleic acid template in the second mixture; and
detecting a condition in the first amplification reaction when the amount of first nucleic acid is not significantly higher (e.g., at least 1.5-fold, 2-fold, 5-fold, 10-fold, 20-fold, etc.) than the amount of second nucleic acid template in the second mixture.

In some embodiments, the second nucleic acid assay is a quantitative hybridization assay. In some embodiments, the reagents for carrying out the second nucleic acid assay include a labeled probe or primer specific for the first nucleic acid template or a complement thereof. In some embodiments, the reagents for carrying out the second nucleic acid assay include a labeled probe or primer specific for the second nucleic acid template or a complement thereof. In some embodiments, the reagents for carrying out the second nucleic acid assay include labeled probes and/or primers specific for the first and second nucleic acid templates.

In some embodiments, the first mixture further comprises a sample (e.g., a biological sample, or other sample suspected of including a nucleic acid of interest). In some embodiments, the first mixture further comprises a set of primers specific for a sample nucleic acid template (e.g., a template included on the suspected nucleic acid of interest). In some embodiments, the sample nucleic acid template includes a genetic variant (e.g., CNV, SNP, or mutation).

Further provided are kits for detecting conditions (e.g., abnormalities or inhibition) in pre-amplification. In some embodiments, the kit comprises a first container with a first set of primers specific for a first nucleic acid template; a second container with a second set of primers specific for a second nucleic acid template, and a third set of primers specific for an amplification product of the first nucleic acid template. In some embodiments, the third set of primers is in the second container. In some embodiments, the container is a well, tube, package, burst pack, or a contained, defined area (e.g., dried on a surface).

In some embodiments, the first and the third sets of primers are different. In some embodiments, the first and third sets of primers are the same. In some embodiments, the kit further comprises a first labeled probe specific for an amplification product of the first nucleic acid template. In some embodiments, the kit further comprises a second labeled probe specific for an amplification product of the second nucleic acid template. In some embodiments, the kit further comprises a first labeled probe specific for an amplification product of the first nucleic acid template and a second labeled probe specific for an amplification product of the second nucleic acid template.

In some embodiments, at least one of the primers in the second set of primers is labeled. In some embodiments, at least one of the primers in the third set of primers is labeled.

In some embodiments, the kit further includes an amplification enzyme. In some embodiments, the kit further includes the first nucleic acid template and the second nucleic acid template, e.g., on the same nucleic acid molecule (single- or double-stranded) or on separate nucleic acid molecules (single- or double-stranded). In some embodiments, the first and second nucleic acid templates are in at least one separate container. In some embodiments, the first and second nucleic acid templates are in the first container.

BRIEF DESCRIPTION OF THE DRAWINGS

FIG. 1A shows C1 and C2 DNA templates with their respective amplification primers. FIG. 1B shows exemplary steps of an embodiment of PASIC. C1 and C2 templates and C1 amplification primers are added to the pre-amplification mix, and amplification is carried out with the C1 template. The downstream analysis is real time PCR, this time with both sets of primers. Because C1 template was pre-amplified, the quantification cycle (Cq) for C1 will be reached before the Cq for C2. FIG. 1C shows that the technique can be carried out with C1 and C2 templates on a single nucleic acid molecule, where the C1 and C2 templates are non-overlapping. FIG. 1D shows that the technique can be carried out with C1 and C2 templates on a single nucleic acid molecule, where the C1 and C2 templates are overlapping. In any of the above aspects, where C1 and C2 templates overlap, intercalating dyes (e.g. SYBR Green) or oligonucleotide probes (e.g., TAQMAN or molecular beacon probes) can be used for qPCR quantification. In aspects where C1 and C2 templates overlap, in embodiments where an oligonucleotide probe is used, one can use separate probes for the C1 and C2 templates, or one can use a common probe that detects both the C1 and C2 template amplicons.

FIGS. 2D and 2E show TBP expression appeared the same in the blood sample and no inhibitor control (traces overlap in FIG. 2D), while TBP expression appeared to be much lower in the chocolate extract sample compared to no inhibitor control (higher Cq1 and Cq2 for chocolate extract in FIG. 2E).

DETAILED DESCRIPTION OF THE INVENTION

A. Introduction

Figure 1A:
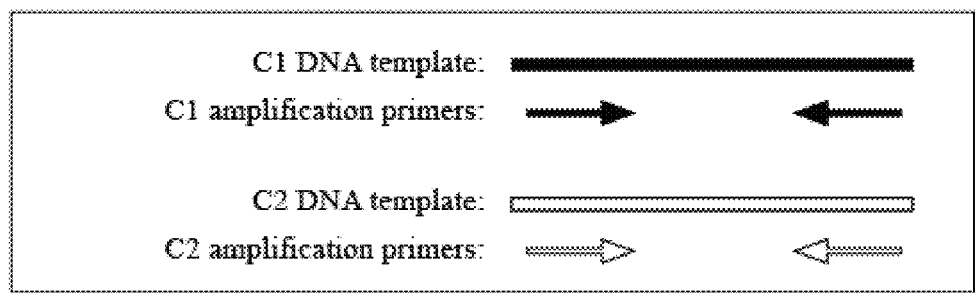
FIGS. 1A, 1B, 1C, and 1D illustrate some embodiments of the PASIC (PreAmp Spike-In Control) technique.
Figure 1B:
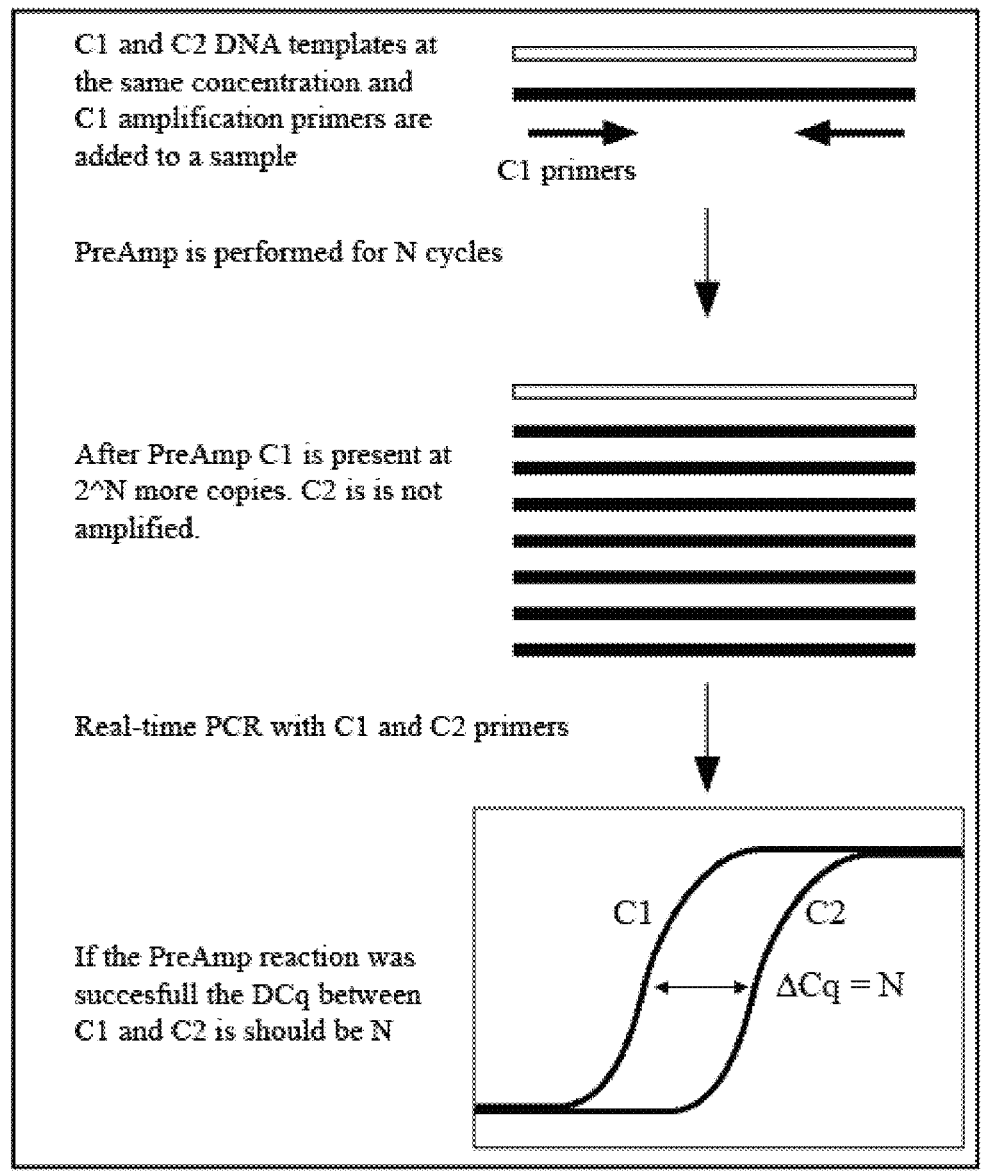
Figure 1C:
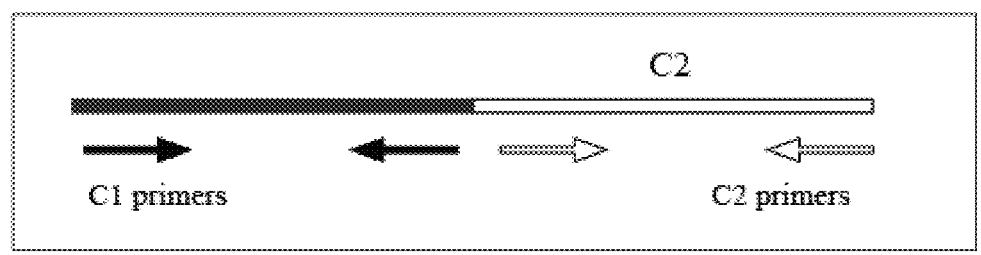
Figure 1D:
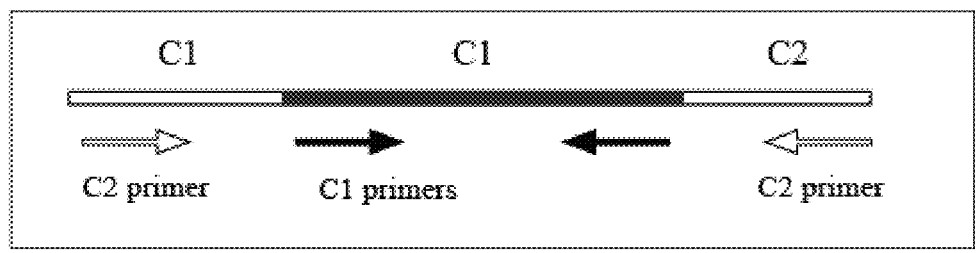
Figure 2A:
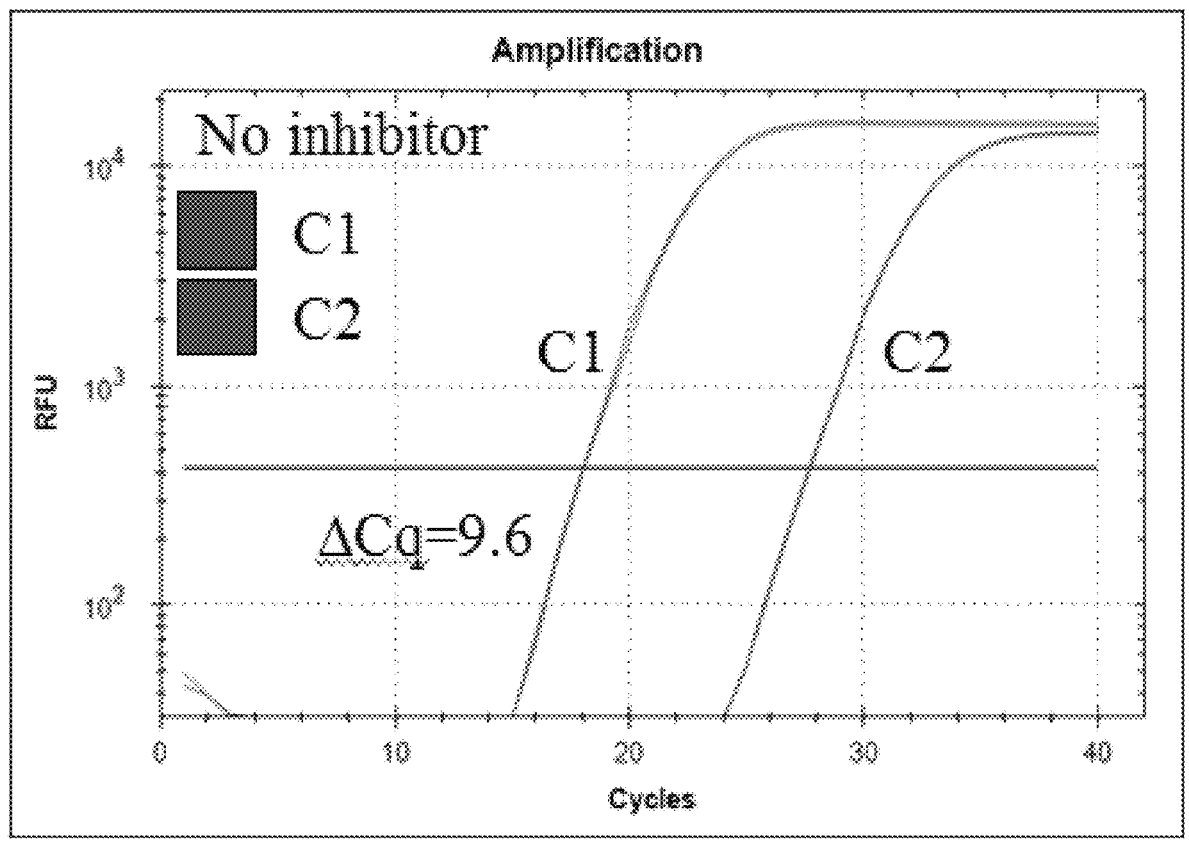
FIGS. 2A, 2B, 2C, 2D, and 2E show representative data using the PASIC technique to amplify TBP (TATA Binding Protein). The Figures show pre-amplification was performed on samples with blood (FIG. 2B) or chocolate extract (FIG. 2C) at levels known to inhibit real time PCR in certain conditions, or a no inhibitor control (FIG. 2A). Pre-amplification was carried out for 10 cycles. Analysis of Cq1 and Cq2 showed that blood did not inhibit pre-amplification, as ΔCq (Cq2-Cq1) was the same as no inhibitor control at 9.6. In contrast, chocolate extract significantly inhibited preamplification such that ΔCq was 0.3. The latter result indicates that C1 template was not significantly amplified during pre-amplification.
Figure 2B:
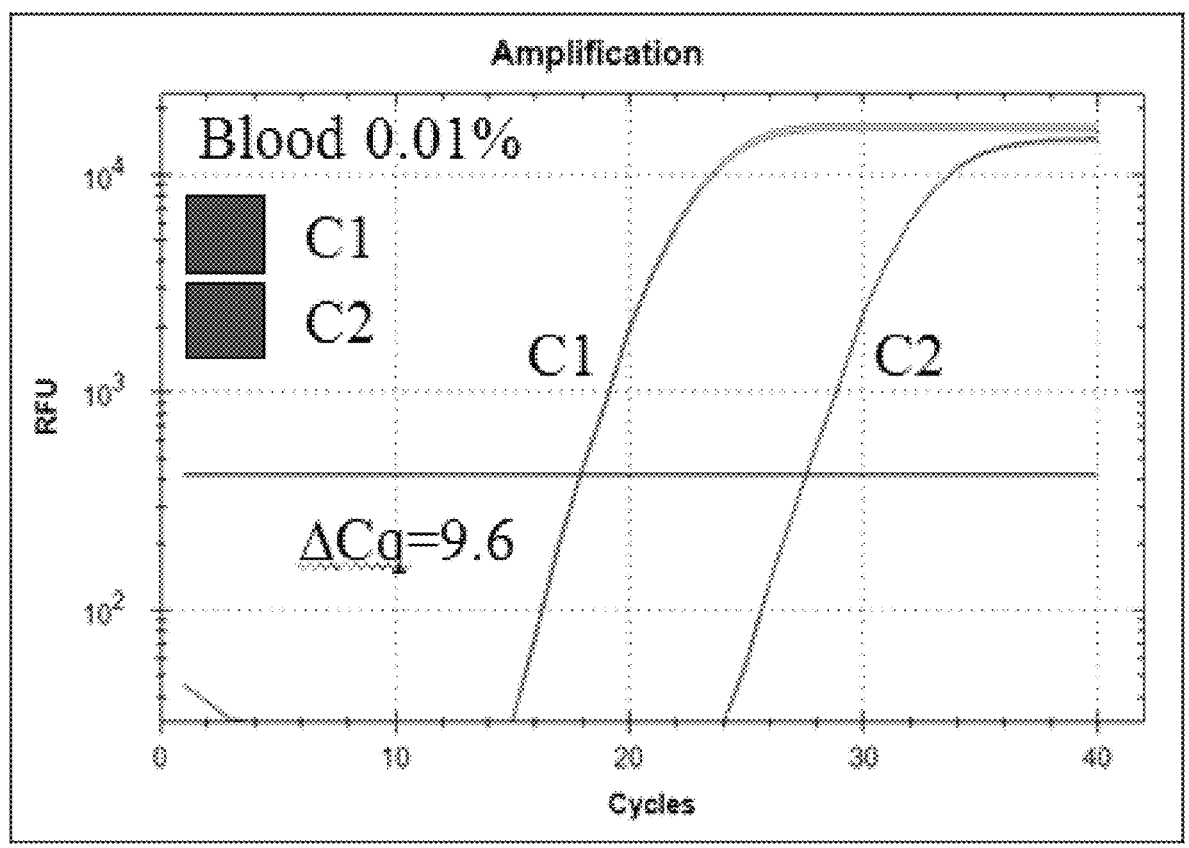
Figure 2C:
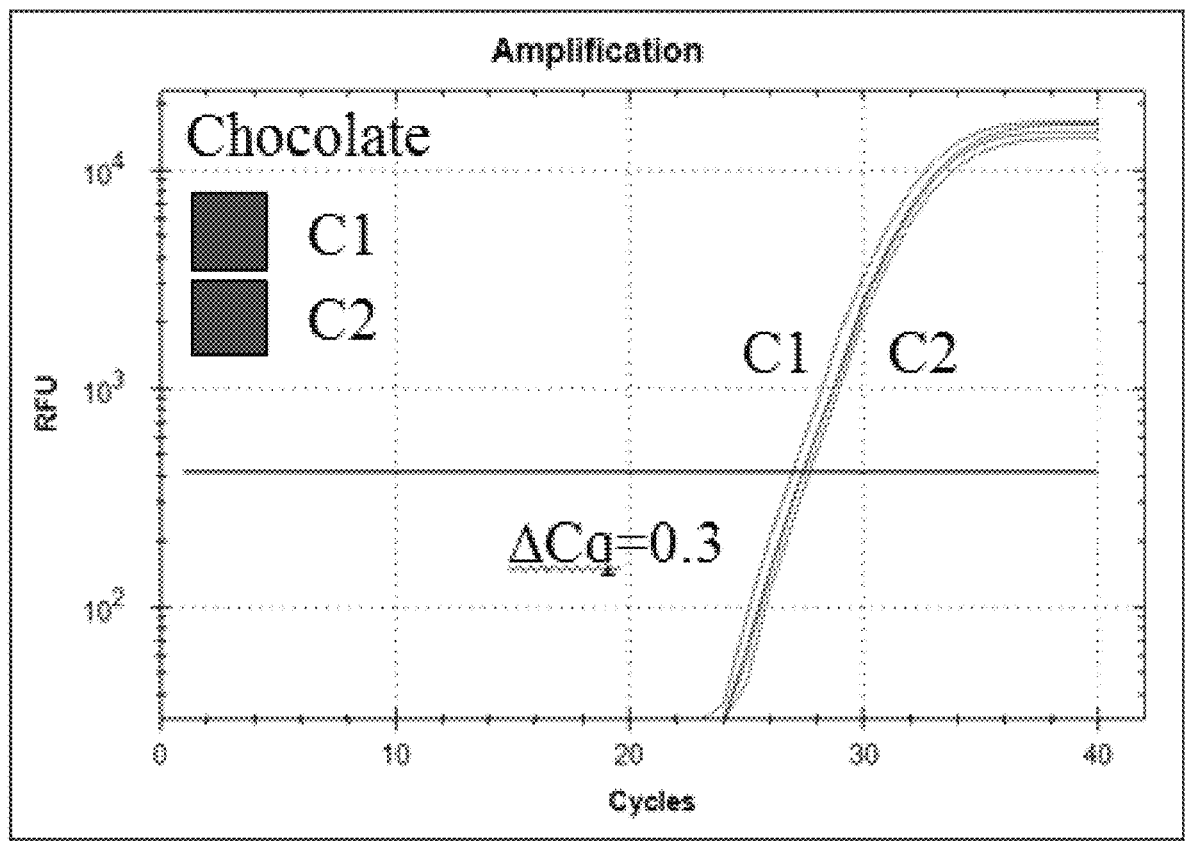
Figure 2D:
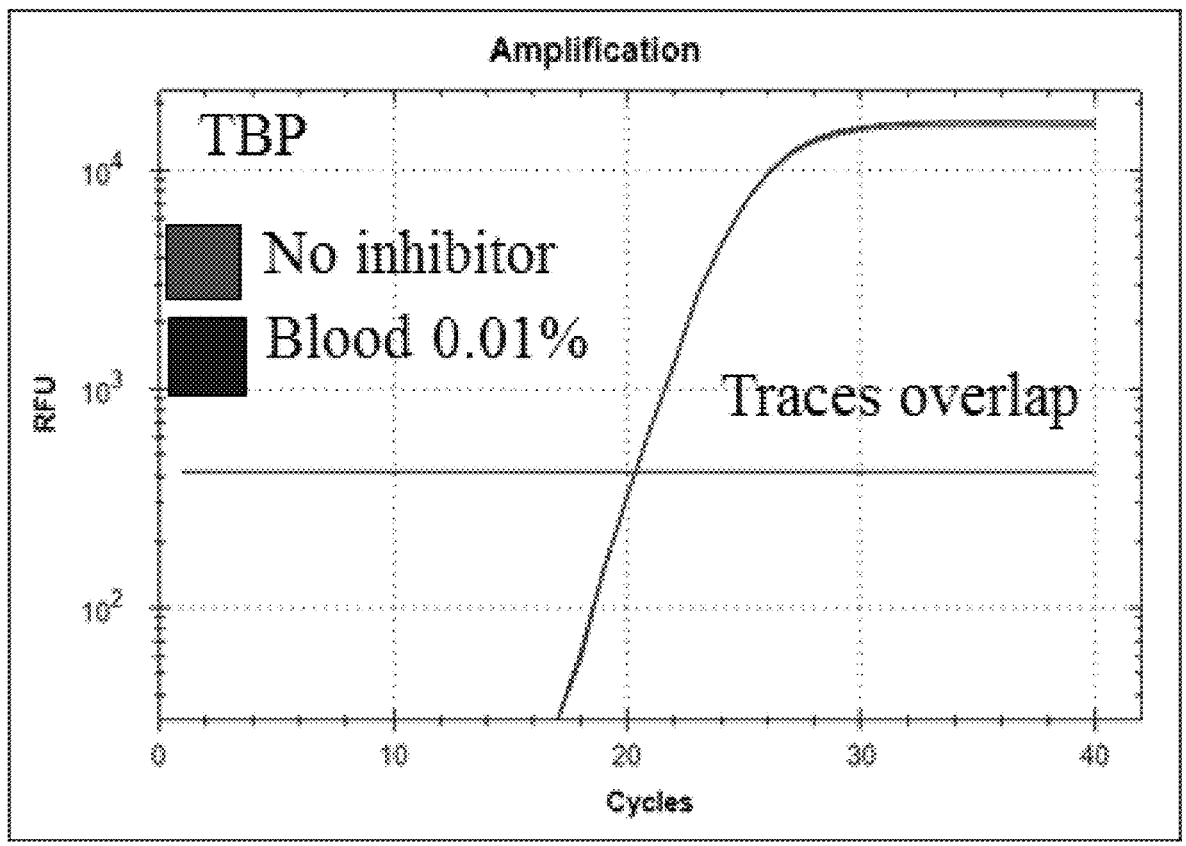
Figure 2E:
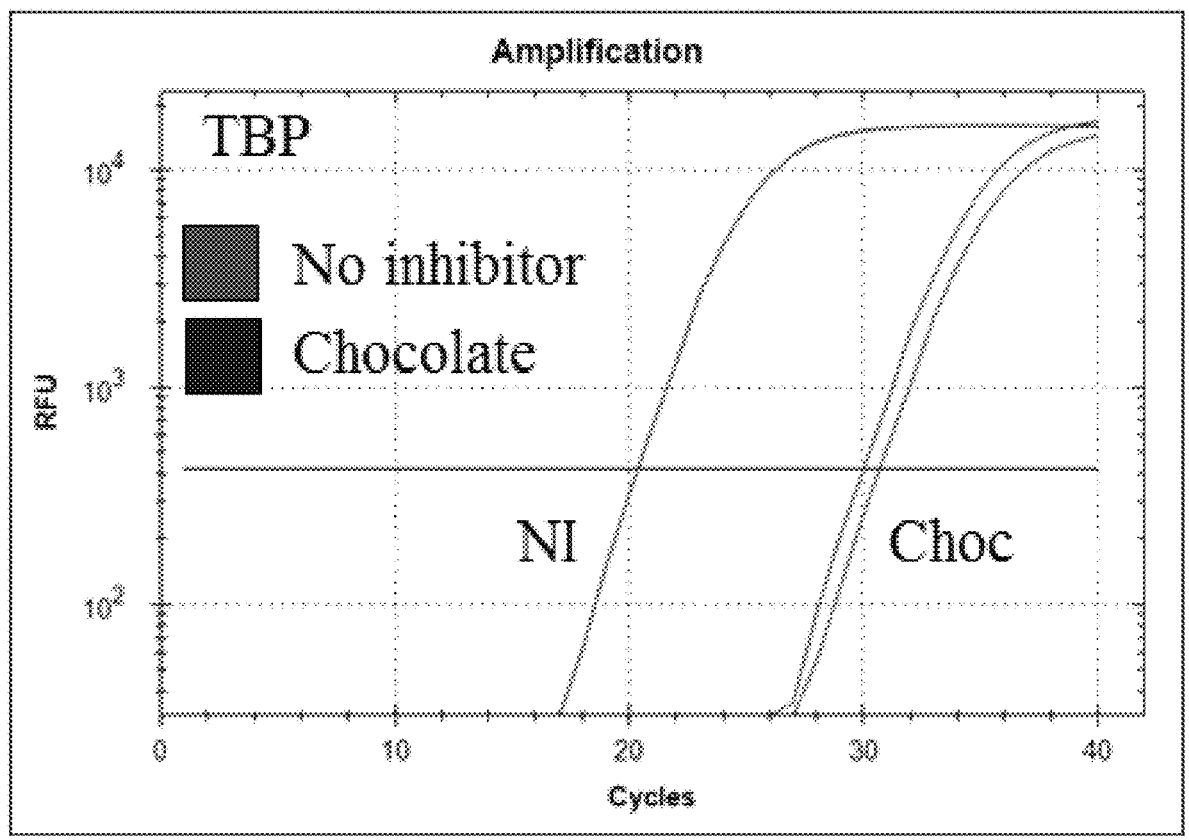

Provided herein are methods and compositions to determine if a pre-amplification reaction is effective, how effective it is, and if there are inhibitory factors present in a particular sample. Pre-amplification is a technique designed to amplify (e.g., by PCR, some other amplification method, or reverse transcription) target nucleic acids prior to downstream analysis. Downstream analysis techniques include quantitative assays such as qPCR (e.g., digital PCR or real time PCR), high resolution melt analysis, molecular beacon assays, hybridization assays, and sequencing reactions.

For example, in a standard nucleic acid analysis, a sample comprising nucleic acids will be mixed with (i) DNA primers designed to amplify a target nucleic acid segment, (ii) a polymerase such as Taq or another amplification enzyme (RNA or DNA polymerase or transcriptase), and (iii) appropriate reagents (e.g., dNTPs, buffer, etc.). After pre-amplification, the product (optionally diluted or processed to separate the amplification product) is added to the downstream analysis reaction. The pre-amplification step increases the amount of the targeted nucleic acid available for further analysis, and is thus useful for detection, quantification, and analysis of rare sequences (e.g., a low copy number mutation).

The present methods and compositions can be used as an internal control for the pre-amplification and later analysis. In such cases, the internal control method is called PASIC (PreAmp Spike-In Control). PASIC can be useful for downstream analyses that involve qPCR, sequencing, detection of expression levels, detection of SNPs, CNVs, or other genetic variants.

When used as an internal control for a sample suspected of having a target nucleic acid to be pre-amplified, (i) first and second known templates (e.g., synthetic or recombinantly produced nucleic acid molecules) are mixed in (spiked in), along with (ii) amplification primers specific for the first template, (iii) amplification primers specific for the target nucleic acid, and (iv) appropriate reagents (e.g., polymerase, dNTPs, buffer, etc.). The pre-amplification reaction is carried out. If there is an inhibitor or some other abnormality in the sample or reaction, the first template will not be amplified as much as would be expected. This can be determined in downstream processing (e.g., a second amplification reaction) as described herein. Detection of an abnormality in amplification of the first template indicates that the targeted nucleic acid in the sample likely was not pre-amplified efficiently either.

In some embodiments, the pre-amplification is of DNA templates, and employs, e.g., PCR. In such cases, the pre-amplification can be run for about 4-24 (e.g., 10-20, 10-24, 5-15, etc.) cycles, depending on the expected concentration of the target nucleic acid, and the amount of first and second template in the reaction. The second template is not amplified in the pre-amplification. Primers specific for both the first and second templates are, however, present in downstream processing steps (e.g., a quantitative amplification reaction).

Assume that the second nucleic acid assay is quantitative PCR, and that the amounts of first and second nucleic acid templates are equal in the first mixture. If the pre-amplification worked perfectly, the number of cycles required in the second amplification to reach a given concentration of second template amplification product would be more than the number of cycles required to reach the same concentration of first template amplification product by the number of pre-amplification cycles. The threshold for determining an "abnormality" can be determined by the user. For example, if pre-amplification is carried out for 10 cycles, the threshold for detecting an abnormality in the second amplification can be set at about 9 cycles (e.g., within about 1 or 2 cycles, 8.5, 8.75, 9.1, 9.2, 9.4, 9.5, 9.6, 9.7, etc.). That is, if the second template amplification product reaches the same concentration as the first template amplification product in less than 9 cycles in the second amplification, the pre-amplification is determined to be abnormal.

The pre-amplification control can be used in multiplex reactions, and in some embodiments, the product from the pre-amplification (first amplification) can be split into multiple "second" nucleic acid assays. For example, the pre-amplification reaction can include multiple sets of amplification primers specific for different target nucleic acids in the sample. In some embodiments, the product of the pre-amplification is split for multiple downstream analyses, e.g., each specific for one or more different target nucleic acids in the sample, as well as the first and second nucleic acid template controls.

For example, a pre-amplification reaction can include elements outlined above: (i) first and second known templates (e.g., in equal or known amounts); (ii) amplification primers specific for the first template, (iii) sample suspected of containing target nucleic acids; (iv) amplification primers specific for the target nucleic acids; and (v) appropriate reagents (amplification enzyme, nucleotides, buffer, etc.). The pre-amplification reaction is then carried out to produce a product. Assuming the pre-amplification worked, and that the sample included at least some of the target nucleic acids, the product would include amplification products of the first nucleic acid template and target nucleic acids from the sample. The product of the first amplification can be added to a single reaction mixture for the second nucleic acid analysis, or can be split between multiple tubes (or wells, containers, or locations) for the second nucleic acid analysis. For example, if the second nucleic acid analysis is qPCR, the reaction mixture can include primers specific for the amplification product of the first nucleic acid template, primers specific for the second nucleic acid template, multiple sets of primers specific for the amplification products of the target nucleic acids, and appropriate reagents. Or the product can be split so that each reaction mixture includes primers specific for the amplification product of the first nucleic acid template, primers specific for the second nucleic acid template, primers specific for just one or a subset of the amplification products of the target nucleic acids from the sample, and appropriate reagents.

In some embodiments, the first amplification is a reverse transcription reaction. In this case, the first nucleic acid template is RNA and the first set of primers can include just one primer, e.g., a poly-T oligonucleotide or an oligonucleotide sequence specific for the known first nucleic acid template. The reverse transcription reaction can include a known first nucleic acid template (RNA), a known second nucleic acid template (RNA or DNA), sample suspected of including target RNA template(s), primer specific for the first nucleic acid template, primer(s) specific for the target RNA templates, and appropriate reagents (e.g., reverse transcriptase, dNTPs, buffer, etc.). In some embodiments, the second nucleic acid analysis is PCR, and the second reaction mixture includes the product of the reverse transcription reaction, primers specific for the amplification product of the first nucleic acid template, primers specific for the second nucleic acid template, primers specific for the amplification product(s) of the target nucleic acids from the sample, and appropriate reagents. Assuming the amount of first RNA template and second nucleic acid template are known in the reverse transcriptase reaction, the threshold for determining an abnormality can be calculated. This variation is also amenable to multiplex assays, where multiple targets from the sample are detected.

The threshold for determining an abnormality in the pre-amplification can be predictably calculated depending on a number of controllable factors. These include, but are not limited to, the relative concentrations of first and second nucleic acid templates in the pre-amplification, the availability of primers specific for each template, the comparative lengths and G-C content of the first and second templates. In some embodiments, the concentration of first and second nucleic acid templates in the pre-amplification is equal (e.g., the two templates are present on a single nucleic acid), the first and second templates are the same length (e.g., about 50-500 nucleotides, 80-150 nucleotides, or about 100-200 nucleotides), or within a few nucleotides (e.g., within 1-10% of the total length). In some embodiments, the G-C content of the first and second nucleic acid templates is the same, or within 2-5 nucleotides.

In some embodiments, the pre-amplification reaction including the first and second known nucleic acid templates, and primers specific for the first nucleic acid template is run alongside the pre-amplification reaction of the sample, e.g., in a separate well of a multiwell plate or in a separate tube. In some embodiments, the pre-amplification reaction including the first and second known nucleic acid templates, and primers specific for the first nucleic acid template is run in a control well for multiple, successive pre-amplification reactions.

If it is determined that the pre-amplification is abnormal where sample is included, the user can go back to the sample and try to separate nucleic acids from the non-nucleic acid material, e.g., with chromatographic methods or by precipitating and resuspending the nucleic acids, or adding an agent to neutralize a suspected contaminant. If the pre-amplification is determined to be abnormal in the absence of sample, the user can check the temperature, humidity, etc. of the amplification instrument. In either case, the user can check to be sure all appropriate reagents were added to the pre-amplification reaction.

B. Definitions

Unless defined otherwise, technical and scientific terms used herein have the same meaning as commonly understood by a person of ordinary skill in the art. Such terms and standard techniques are described, e.g., in Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989); Oligonucleotide Synthesis (Gait, ed., Current Edition); Nucleic Acid Hybridization (Hames & Higgins, eds., Current Edition); Transcription and Translation (Hames & Higgins, eds., Current Edition); CRC Handbook of Parvoviruses, Vol. I & II (Tijessen, ed.); Fundamental Virology, 2nd Edition, Vol. I & II (Fields and Knipe, eds.)). The term "a" or "an" is intended to mean "one or more." The term "comprise" and variations thereof such as "comprises" and "comprising," when preceding the recitation of a step or an element, are intended to mean that the addition of further steps or elements is optional and not excluded. The following definitions are provided to facilitate understanding of certain terms used frequently herein and are not meant to limit the scope of the present disclosure.

As used herein, a "condition" or an "abnormality" in an amplification reaction refers to any factor that results a level of amplification that is less than anticipated given known template, template concentration, and amplification conditions. Examples include factors that inhibit amplification, e.g., interfere with or reduce the activity of the amplification enzyme or interfere with the primers or template. Abnormalities can also result from problems with the instrument or reaction (e.g., denaturization temperature not reached, etc.) that will affect the amplification. Unless otherwise specified, an abnormality will not refer to issues specific to pre-amplification of a targeted sample nucleic acid, e.g., chromatin interference with intended template or repeat sequences in the sample template that are difficult to amplify.

A "cycle" refers to an amplification cycle, which typically includes primer hybridization to a template nucleic acid, primer extension/polymerization, and denaturation of the template and newly-formed strand. In PCR, each cycle results in doubling of the amount of template, and repeated cycling results in exponential amplification of the template ([template]$\times 2^n$, where n=number of cycles).

The term "quantification cycle" (Cq) refers to the number of cycles needed to reach a set threshold fluorescence signal, e.g., the quantitative zone of a quantitative amplification reaction. The level of the threshold is selected to capture data during the exponential phase of the reaction. To determine Cq values, background fluorescence levels can be subtracted from the raw fluorescence data. Background can be based on the initial, stable fluorescence level in the first few cycles, before detectable amplification. In some embodiments, fluorescence threshold is selected using an instrument specific algorithm, or manually. Data analysis searches data curves for each sample and interpolates a Cq value for that sample crossing the threshold. The specific Cq is a relative value, relative to the starting template copy number, and specific for the instrument, reagents, efficiency of the amplification, sensitivity of the reaction, etc. A lower Cq indicates higher amount of starting template, more efficient amplification, etc.

As used herein, a "sample" refers to a specimen suspected of carrying a nucleic acid of interest. The sample can be a biological sample, or retrieved from the environment, e.g., swabbed from a surface, a food sample, from a water treatment facility, etc. The sample can be processed prior to assay, e.g., to remove non-nucleic acid debris. The term encompasses samples that have been manipulated after their procurement, such as by treatment with reagents, solubilization, sedimentation, or enrichment for certain components. The nucleic acid of interest can be a genetic variant (e.g., a copy number variant, polymorphism, or mutation), an expression product (e.g. RNA or amplification product thereof), or from an infectious agent (e.g., bacteria, phage, virus, or fungus).

A "threshold" as described herein refers to a number selected by the user based on the conditions of the particular assay for determining that a pre-amplification reaction is somehow abnormal, e.g., less than optimal or less than expected given the conditions that can be controlled for (e.g., template concentrations and lengths, primer concentrations, etc.). In some embodiments, the threshold refers to the tolerated difference between the ΔCq for amplifications of a first and second template and a known number of amplification cycles (e.g., the number of cycles in a pre-amplification step). In some embodiments, the threshold refers to the tolerated difference between the amounts of first and second nucleic acids in a reaction, e.g., as determined in a quantitative hybridization or sequencing reaction. In some embodiments, the threshold refers to the tolerated difference between the expected difference between the amounts of first and second nucleic acids in a reaction and the actual amounts determined in a quantitative assay. In some embodiments, the threshold allows for 1-20% variation from the expected value (e.g., 1-10%, 1-5%, 5-10% variation). For example, if the expected ΔCq for amplifications of a first and second template is 10, the threshold for determining that there is an abnormality can be set at 0.1-2 cycles, e.g., about 0.5 cycles.

The term "biological sample" encompasses a variety of sample types obtained from an organism. The term encompasses bodily fluids such as blood, blood components, saliva, serum, plasma, urine and other liquid samples of biological origin, solid tissue biopsy, tissue cultures, or supernatant taken from cultured cells. The biological sample can be processed prior to assay, e.g., to remove cells or cellular debris. The term encompasses samples that have been manipulated after their procurement, such as by treatment with reagents, solubilization, sedimentation, or enrichment for certain components.

A "control," "control sample," "standard control," or "control value" refers to a sample that serves as a reference, usually a known reference, for comparison to a test sample. For example, a test sample can be taken from a patient suspected of having a disease or carrying a polymorphism, and compared to samples from a known disease patients, known polymorphism carriers, or a known normal (non-disease) individual. A control can also represent an average value gathered from a population of similar individuals, e.g., patients or healthy individuals with a similar medical background, same age, weight, etc. A control value can also be obtained from the same individual, e.g., from an earlier-obtained sample, prior to disease, or prior to treatment. An "internal control" is a control for a reaction or assay that is carried out concurrently with, typically in the same tube, well, surface, or container as the reaction or assay being tested. The internal control can be used to detect abnormalities within the sample. For example, an internal control for a PCR reaction to detect a nucleic acid in a sample could include known PCR primers and template that will be amplified absent inhibitors or some other abnormality in the reaction.

One of skill will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "nucleic acid" refers to deoxyribonucleotides or ribonucleotides and polymers thereof in either single- or double-stranded form, and complements thereof. "Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. The term "nucleotide" typically refers to a single unit of a polynucleotide, i.e., a monomer. Nucleotides can be ribonucleotides, deoxyribonucleotides, or modified versions thereof.

A "nucleic acid template" refers to a single or double stranded nucleic acid molecule that encompasses a targeted sequence, e.g., a sequence to be amplified or otherwise detected. For example, a nucleic acid template can be defined by the sequences that hybridize to a 5' PCR primer and 3'PCR primer. A nucleic acid template can be longer than the detected portion, e.g., when it is detected by a probe representing a subsequence of the nucleic acid template. A given nucleic acid template, e.g., defined by amplification primers, can include genetic variants that can be the focus of downstream analysis (e.g., detection, quantification, sequencing, etc.).

As used herein, a "genetic variant" refers to a mutation, single nucleotide polymorphism (SNP), deletion variant, missense variant, insertion variant, inversion, or copy number variant (CNV). A genetic variant can be used as a biomarker, and can result in increased or decreased expression levels, or differential modification.

The present disclosure includes polynucleotides and polypeptides that have substantially similar sequence identity to known markers or sequences. As used herein, two polynucleotides or polypeptides have "substantial sequence identity" when there is at least about 70% sequence identity, at least about 80% sequence identity, at least about 90% sequence identity, at least about 95% sequence identity, at least about 99% sequence identity, or 100% sequence identity between their amino acid sequences, or when polynucleotides (e.g., polynucleotides encoding the polypeptides) are capable of forming a stable duplex with each other under stringent hybridization conditions or conditions defined by the practitioner. One of skill will recognize that a genetic variant can be detected in a sequence that is less than a full length gene sequence, or outside a defined gene sequence, e.g., using PCR to amplify a fragment that includes the genetic variant site or a probe that is complementary to a sequence that includes the genetic variant site. Where the aspects or embodiments refer to sequence identity, that sequence identity can be with respect to a portion of the sequence as disclosed herein (e.g. 15, 20, 25, 30, 35, 40, 45, 50, 60, 70, 80, 90, 100, 200, 500, 1000 or more nucleic acid bases or amino acids in length).

The terms "probe" or "primer" refer to one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes are more often longer, e.g., 25-100 or more than a hundred nucleotides, e.g. 100-500 nucleotides in length. The probe or primers can be unlabeled or labeled as described below so that its binding to a target sequence can be detected (e.g., with a fluorophore. The probe or primer can be designed based on one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization and detection procedures, and to provide the required resolution among different genes or genomic locations.

Probes and primers can also be immobilized on a solid surface (e.g., nitrocellulose, glass, quartz, fused silica slides), as in an array. Techniques for producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of particular probes and primers can be modified from the target sequence to a certain degree to produce probes that are "substantially identical" or "substantially complementary to" a target sequence, but retain the ability to specifically bind to (i.e., hybridize specifically to) the same targets from which they were derived.

A probe or primer is "specific for" or "capable of detecting" a nucleic acid sequence or genetic variant if it is substantially complementary to the sequence or a region that covers or is adjacent to the genetic variant. For example, to detect a SNP, primers can be designed on either side of the SNP, and primer extension used to determine the identity of the nucleotide at the position of the SNP. In some embodiments, a probe is used in conditions such that it hybridizes only to a genetic variant, or only to a dominant sequence.

Again, in the context of nucleic acids, the term "capable of hybridizing to" refers to a polynucleotide sequence that forms Watson-Crick bonds with a complementary sequence. One of skill will understand that the percent complementarity need not be 100% for hybridization to occur, depending on the length of the polynucleotides, length of the complementary region (e.g. 5, 10, 15, 20, 25, 30, 35, 40, 45, 50, 60, 70, 80, 90, 100, or more bases in length), and stringency of the conditions. For example, a polynucleotide (e.g., primer or probe) can be capable of binding to a polynucleotide having 60%, 65%, 70%, 75%, 80%, 85%, 90%, 91%, 92%, 93%, 94%, 95%, 96%, 97%, 98%, 99% or 100% complementarity over the stretch of the complementary region. In the context of detecting genetic variants, the tolerated percent complementarity or number of mismatches will vary depending on the technique used for detection (see below).

A "hybridization assay" is an assay that relies on Watson-Crick binding between complementary nucleic acid strands. The hybridization can involve primer(s) (e.g., in an amplification or sequencing reaction) or probe(s) (e.g., a molecular beacon, or interacting FRET probes). In some embodiments, the primer(s) and/or probe(s) are labeled. In some embodiments, the hybridization assay includes use of intercalating dyes.

In the context of nucleic acids, the term "amplification product" refers to a nucleic acid (e.g., polynucleotide) that results from an amplification reaction, e.g., PCR and variations thereof, reverse transcription, strand displacement reaction (SDR), ligase chain reaction (LCR), transcription mediated amplification (TMA), or Qbeta replication. A thermally stable polymerase, e.g., Taq, can be used to avoid repeated addition of polymerase throughout amplification procedures that involve cyclic or extreme temperatures (e.g., PCR and its variants).

Unless otherwise specified, the term "reagent" is used broadly to include assay components, including enzymes, antibodies, probes, binding agents (e.g., receptor or target), samples, wash fluids, buffers, detection agents, etc.

The terms "label," "detectable moiety," "detectable agent," and like terms refer to a composition detectable by spectroscopic, photochemical, biochemical, immunochemical, chemical, or other physical means. For example, useful labels include fluorescent dyes, luminescent agents, radio-isotopes (e.g., $^{32}$P, $^3$H), electron-dense reagents, enzymes, biotin, digoxigenin, or haptens and proteins or other entities which can be made detectable, e.g., by affinity. Any method known in the art for conjugating a nucleic acid or other biomolecule to a label may be employed, e.g., using methods described in Hermanson, *Bioconjugate Techniques* 1996, Academic Press, Inc., San Diego. The term "tag" can be used synonymously with the term "label," but generally refers to an affinity-based moiety, e.g., a "His tag" for purification, or a "strepavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule. The signal from the label can be indicative of the amount of the labeled molecule.

Forster resonance energy transfer (abbreviated FRET), also known as fluorescence resonance energy transfer, is a mechanism describing energy transfer between two chromophores. A donor chromophore (FRET donor), initially in its electronic excited state, can transfer energy to an acceptor chromophore (FRET acceptor), which is typically less than 10 nm away, through nonradiative dipole-dipole coupling. The energy transferred to the FRET acceptor is detected as an emission of light (energy) when the FRET donor and acceptor are in proximity. A "FRET signal" is thus the signal that is generated by the emission of light from the acceptor. The efficiency of Forster resonance energy transfer between a donor and an acceptor dye separated by a distance of R is given by $E=1/[1+(R/R_0)^6]$ with $R_0$ being the Förster radius of the donor-acceptor pair at which $E=\frac{1}{2}$. $R_0$ is about 50-60 Å for some commonly used dye pairs (e.g., Cy3-Cy5). FRET signal varies as the distance to the $6^{th}$ power. If the donor-acceptor pair is positioned around $R_0$, a small change in distance ranging from 1 Å to 50 Å can be measured with the greatest signal to noise. With current technology, 1 ms or faster parallel imaging of many single FRET pairs is achievable.

A "FRET pair" refers to a FRET donor and FRET acceptor pair that are capable of FRET detection.

The terms "fluorophore," "dye," "fluorescent molecule," "fluorescent dye," "FRET dye" and like terms are used synonymously herein unless otherwise indicated.

C. Amplification Reactions

The presently disclosed assays and methods can include use of a range of nucleic acid amplification reactions, e.g., PCR and variations thereof (e.g. TaqMan, real time PCR, quantitative PCR), reverse transcription, strand displacement reaction (SDR), ligase chain reaction (LCR), transcription mediated amplification (TMA), or Qbeta replication. A thermally stable polymerase, e.g., Taq, can be used to avoid repeated addition of polymerase throughout amplification procedures that involve cyclic or extreme temperatures (e.g., PCR and its variants). Such methods are known in the art, for example, a side-by-side comparison of PCR, LCR, TMA, and SDR for detection of *Chlamydia* is provided in Gaydos et al. (2004) *J. Clin. Microbiol.* 42:3041.

Polymerase chain reaction (PCR) is the most commonly used technique. PCR is capable of producing large amounts of specific DNA fragments with length and sequence defined by a nucleic acid template and 5' and 3' primers. The essential steps include thermal denaturation of a double-stranded target nucleic acid, annealing of the primers to their complementary sequences, and extension of the annealed primers by enzymatic synthesis with DNA polymerase. Taq or another thermostable polymerase (e.g. Pfu, Paq5000, Phusion DNA polymerase) can be used. The portion to be amplified (template) is defined by where the primers bind to the target nucleic acid. See e.g., Dieffenbach & Dveksler *PCR Primer: A Laboratory Manual* (Cold Spring Harbor Laboratory Press 2003).

Quantitative PCR (qPCR) is used to amplify and simultaneously quantify one or more targeted nucleic acid templates. The quantity can be either an absolute number of copies or a relative amount when normalized to a known DNA input (e.g., an internal or external control) or additional normalizing genes (e.g., housekeeping gene such as β-actin). Two common methods for qPCR detection are: (1) non-specific fluorescent dyes that intercalate with double-stranded DNA, and (2) sequence-specific probe(s) labeled with a fluorescent reporter which permits detection only after hybridization of the probe (e.g., molecular beacon).

Reverse transcription can be used to amplify an RNA template. In this case, reverse transcriptase and dNTPs are included with a primed RNA molecule to produce cDNA. In embodiments where the first amplification reaction is reverse transcription, the "first set of primers" may include only one primer, e.g., a poly-T oligonucleotide, or a primer that hybridizes to a known sequence on the template transcript or other template RNA molecule. The single stranded cDNA produced by reverse transcription is then used for subsequent PCR. This method can be referred to as RT-PCR (reverse transcriptase PCR), not to be confused with real time PCR, which can be referred to with the same acronym.

Transcription mediated amplification (TMA) is a method that uses RNA transcription (RNA polymerase) and DNA synthesis (reverse transcriptase) to produce RNA amplicon from a target nucleic acid. TMA can be used to target both RNA and DNA. TMA is isothermal and can produce 100-1000 copies per cycle in contrast to PCR, which produces only two copies per cycle. This can result in a 10 billion fold increase of copies within about 15-30 minutes. TMA also produces RNA amplicon rather than DNA amplicon. See, e.g., Kamisango et al. (1999) *J. Clin. Microbiol.* 37:310.

LCR is a DNA amplification technique based upon the ligation of adjacent nucleic acid probes. The probes are designed to exactly match two adjacent sequences of a specific target DNA. The chain reaction is repeated in three steps in the presence of excess probe: (1) heat denaturation of double-stranded DNA, (2) annealing of probes to target DNA, and (3) joining of the probes by thermostable DNA ligase. After the reaction is repeated (e.g., for 20-30 cycles) the production of ligated probe is measured.

Real time PCR and the 5'-nuclease activity of Taq DNA polymerase can be used for detecting genetic variants. The assay requires forward and reverse PCR primers that will amplify a region that includes a variant site. Variant discrimination can be achieved using FRET, and one or two allele-specific probes that hybridize to the variant site. The probes have a fluorophore linked to their 5' end and a quencher molecule linked to their 3' end. While the probe is intact, the quencher will remain in close proximity to the fluorophore, eliminating the fluorophore's signal. During the PCR amplification step, if the variant-specific probe is perfectly complementary to the variant allele, it will bind to the target DNA strand and then get degraded by 5'-nuclease activity of the Taq polymerase as it extends the DNA from the PCR primers. The degradation of the probe results in the separation of the fluorophore from the quencher molecule, generating a detectable signal. If the variant-specific probe is not perfectly complementary, it will have lower melting temperature and not bind as efficiently. This prevents the nuclease from acting on the probe.

In digital PCR (dPCR, or droplet digital PCR, ddPCR), a sample is diluted and partitioned into multiple (hundreds or even millions) separate reaction chambers so that each contains one or no copies of the sequence of interest. By counting the number of positive partitions (in which the sequence is detected) versus negative partitions (in which it is not), one can determine exactly how many copies of a DNA molecule were in the original sample (see, e.g., Sykes et al. (1992) *Biotechniques* 13:444; Baker (2012) *Nature Methods* 9:541). Because of its extraordinary sensitivity, dPCR can be used to distinguish differential expression of alleles or disease genes, viral levels, or to detect fetal DNA in circulating blood. While simple in concept, dPCR typically relies on nanofabrication and microfluidic devices, e.g., from Bio-Rad®, Fluidigm®, RainDance®, and Life Technologies®.

Förster resonance energy transfer (FRET) detection can be used for detection in primer extension and ligation reactions where the two labels are brought into close proximity to each other. It can also be used in the 5'-nuclease reaction, the molecular beacon reaction, and the invasive cleavage reactions where the neighboring donor/acceptor pair is separated by cleavage or disruption of the stem-loop structure that holds them together. FRET occurs when two conditions are met. First, the emission spectrum of the fluorescent donor dye must overlap with the excitation wavelength of the acceptor dye. Second, the two dyes must be in close proximity to each other because energy transfer drops off quickly with distance. The proximity requirement is what makes FRET a good detection method for a number of allelic discrimination mechanisms.

A variety of dyes can be used for FRET, and are known in the art. The most common ones are fluorescein, cyanine dyes (Cy3 to Cy7), rhodamine dyes (e.g. rhodamine 6G), the Alexa series of dyes (Alexa 405 to Alexa 730). Some of these dyes have been used in FRET networks (with multiple donors and acceptors). Optics for imaging all of these require detection from UV to near IR (e.g. Alex 405 to Cy7), and the Atto series of dyes (Atto-Tec GmbH). Example dye pairs for FRET labeling include Alexa-405/Alex-488, Alexa-488/Alexa-546, Alexa-532/Alexa-594, Alexa-594/Alexa-680, Alexa-594/Alexa-700, Alexa-700/Alexa-790, Cy3/Cy5, Cy3.5/Cy5.5, and Rhodamine-Green/Rhodamine-Red, etc. Fluorescent metal nanoparticles such as silver and gold nanoclusters can also be used (Richards et al. (2008) *J Am Chem Soc* 130:5038-39; Vosch et al. (2007) *Proc Natl Acad Sci USA* 104:12616-21; Petty and Dickson (2003) *J Am Chem Soc* 125:7780-81 Available filters, dichroics, multichroic mirrors and lasers can affect the choice of dye.

D. Additional Nucleic Acid Assays

The presently disclosed pre-amplification verification methods can be used in combination with amplification reactions, or with other nucleic acid analyses, such as high resolution melt (HRM) assays, molecular beacon assays, and nucleic acid sequencing. Such methods can be used to detect genetic variants such as single nucleotide polymorphisms (SNPs), allelic differences (zygosity), and mutations.

HRM assays typically involve use of intercalating dyes that bind to double stranded DNA and fluoresce as long as the molecule remains double stranded. The double stranded DNA sample is gradually heated until the strands melt, and fluorescence decreases. Intercalating dyes that can be used in these assays include, for example, SYBR® Green, LC Green, LC Green Plus, ResoLight, EvaGreen®, Chromofy, GreenER™, and SYTO 9.

HRM assays can be used to detect mutations, zygosity, and SNPs. For example, if primers used in the pre-amplification straddle the point of allelic difference in a genetic sequence, two amplification products will be produced, one for each allele. Homozygotes for either allele will have higher melting temperature (later reduction in fluorescence) than heterozygotes, because essentially all nucleic acid strands will be 100% hybridized (accounting for some small percentage of inaccuracy by the amplification enzyme). In heterozygotes, a more significant percentage of amplification products will hybridize with a mismatch at the site of allelic difference.

Such methods are described, e.g., in Reed et al. (2007) *Pharmacogenetics* 8:597; Krypuy et al. (2007) *BMC Cancer* 7:168. HRM can also be used to detect methylation, as described, e.g., in Wojdacz & Dobrovic (2007) *Nucl. Acids Res.* 35:e41, and to distinguish between samples as described, e.g., in Zianni et al. (2013) *J. Biomol. Tech.* 24:1.

Molecular beacons can also be used to detect genetic variants such as mutations, zygosity, and SNPs. This method makes use of a specifically engineered single-stranded oligonucleotide probe. The oligonucleotide is designed such that there are complementary regions at each end and a probe sequence located in between. This design allows the probe to take on a hairpin, or stem-loop, structure in its natural, isolated state. Attached to one end of the probe is a fluorophore and to the other end a fluorescence quencher. Because of the stem-loop structure of the probe, the fluorophore is in close proximity to the quencher, thus preventing the molecule from emitting any fluorescence. The molecule is also engineered such that only the probe sequence is complementary to the targeted genomic DNA sequence.

If the probe sequence of the molecular beacon encounters its target genomic DNA sequence during the assay, it will anneal and hybridize. Because of the length of the probe sequence, the hairpin segment of the probe will be denatured in favor of forming a longer, more stable probe-target hybrid. This conformational change permits the fluorophore and quencher to be free of their tight proximity due to the hairpin association, allowing the molecule to fluoresce.

If on the other hand, the probe sequence encounters a target sequence with as little as one non-complementary nucleotide, the molecular beacon will preferentially stay in its natural hairpin state and no fluorescence will be observed, as the fluorophore remains quenched. The design of molecular beacons allows for a simple diagnostic assay to identify mismatches at a given location. If one molecular beacon is designed to match a wild-type allele and another to match a mutant of the allele, the two can be used to identify the genotype of an individual. If only the first probe's fluorophore wavelength is detected during the assay then the individual is homozygous to the wild type. If only the second probe's wavelength is detected then the individual is homozygous to the mutant allele. Finally, if both wavelengths are detected, then both molecular beacons must be hybridizing to their complements and thus the individual must contain both alleles and be heterozygous.

E. Threshold Calculations

Calculations for the methods described herein can involve computer-based calculations and tools. For example, the concentration of a given nucleic acid (or difference between the concentrations of two or more nucleic acids), or the Cq of an amplification reaction (or $\Delta$Cq of two or more amplification reactions) can be compared by a computer to a threshold value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VB Script, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. Software tools can be implemented as scripts (e.g., using PERL), execution of which can be initiated by a user from a standard command line interface of an operating system such as Linux or UNIX. Commands can be adapted to the operating system as appropriate. In other embodiments, a graphical user interface may be provided, allowing the user to control operations using a pointing device. Thus, the presently disclosed methods are not limited to use with any particular user interface.

Scripts or programs incorporating data points and calculations as disclosed herein can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

F. Kits

Further provided are kits including components for use in PASIC. In some embodiments, the kit provides internal control components to establish the efficacy of a pre-amplification reaction.

The kit can include (e.g., in separate containers, separated compartments, wells, tubes, packages, burst packs, or a contained, defined areas (e.g., dried on a surface)) (i) a first set of primers specific for a first nucleic acid template; (ii) a second set of primers specific for a second nucleic acid template; and (iii) a third set of primers specific for an amplification product of the first nucleic acid template. The first and third sets of primers can be the same, and in that case, included in the same container or compartment. The first and third sets of primers can also be different, e.g., hybridizing to different or overlapping sequences on the first nucleic acid template or differently labeled. The kit can further include (iv) a nucleic acid (DNA or RNA) comprising the first nucleic acid template; (v) a nucleic acid (DNA or RNA) comprising the second nucleic acid template. In some cases, components (iv) and (v) are present in equal amounts in the same container/compartment, or both the first and second nucleic acid templates are on the same nucleic acid.

The kit can also include (vi) a first labeled probe specific for an amplification product of the first nucleic acid template and/or (vii) a second labeled probe specific for an amplification product of the second nucleic acid template.

The kit can also include reagents for carrying out the pre-amplification and downstream analyses, e.g., amplification enzyme(s) (Taq, reverse transcriptase, or other RNA or DNA polymerases), buffers, single nucleotide mixes, intercalating dyes, etc. The kit can also include consumables for carrying out the pre-amplification and downstream analyses, e.g., multiwell plates, tubes, cuvettes, pipettes, etc. The kit can also include amplification inhibitor, e.g., as a control to aid in setting a threshold for determining abnormality in a pre-amplification reaction.

G. Examples

Example 1

Materials
Tube 1 (50×): Template 1+S1 primers (2.5-5 uM)
Template 2 (same concentration as Template 1)
qPCR mixture: S1 primers+S2 primers+amplification enzyme Protocol
Spike 1 uL of Tube 1 into Pre-amplification reaction including sample, and perform pre-amplification reaction for N cycles. Perform qPCR (quantitative PCR) using pre-amplification product. Cq of Template 1 (Cq1) is ~N cycles less than Cq of Template 2 (Cq2), indicating no abnormality in the pre-amplification reaction. Optional controls: (1) Spike 1 uL of Tube 1 into qPCR without pre-amplification. Cq1 and Cq2 should be the same (barring thermodynamic difference between amplifications of T1 and T2); (2) Perform pre-amplification without sample, followed by qPCR. Cq1 and Cq2 should be the same, unless the sample includes inhibitory factor(s).

Features
The method demonstrates whether, and to what extent, pre-amplification worked. Tube 1 can be used as an internal control, e.g., to calibrate reactions run in successive multiwell plates. The presence of inhibitory factor(s) can be detected for each sample.

Example 2

Materials
Tube 1 (50×): 180mer DNA including Sp-1 and Sp-2 target template sequences
Sp-1 primers (2.5-5 uM)
Tube 2: Sp-1 qPCR primers (20×)
Tube 3: Sp-2 qPCR primers (20×)

Protocol
Spike 1 uL of Tube 1 into Pre-amplification reaction including sample, and perform pre-amplification reaction for N cycles. Perform qPCR with 1 uL each of Tube 2 and Tube 3 using pre-amplification product. Cq of Template 1 (Cq1) is ~N cycles less than Cq of Template 2 (Cq2), indicating no abnormality in the pre-amplification reaction. Optional controls: (1) Spike 1 uL of Tube 1 into qPCR without pre-amplification. Cq1 and Cq2 should be the same (barring thermodynamic difference between amplifications of T1 and T2); (2) Perform pre-amplification without sample, followed by qPCR. Cq1 and Cq2 should be the same, unless the sample includes inhibitory factor(s).

Features
The method demonstrates whether, and to what extent, pre-amplification worked. Tube 1 can be used as an internal control, e.g., to calibrate reactions run in successive multiwell plates. The presence of inhibitory factor(s) can be detected for each sample. In addition, because both control templates are on one nucleic acid, the template concentrations will necessarily be the same.

The above disclosure is provided to illustrate the invention but not to limit its scope. Variants of the invention will be readily apparent to one of ordinary skill in the art and are encompassed by the appended claims. All publications, databases, interne sources, patents, patent applications, and accession numbers cited herein are hereby incorporated by reference in their entireties for all purposes.

What is claimed is:

1. A kit comprising:
 a first container containing a first nucleic acid template, a second nucleic acid template, and a set of primers specific for the first nucleic acid template, such that when the mixture in the first container is exposed to amplification conditions, a first nucleic acid template amplification product, but not a second nucleic acid template amplification product is formed; and
 a second container containing a set of primers specific for the second nucleic acid template, and a set of primers specific for the first nucleic acid template amplification product,
 wherein: (i) at least one of the primers in one of the sets is labeled, (ii) the kit comprises an intercalating dye, or (iii) the kit comprises a first labeled probe specific for an amplification product of the first nucleic acid template and/or a second labeled probe specific for an amplification product of the second nucleic acid template.

2. The kit of claim 1, wherein the set of primers specific for the first nucleic acid template and the set of primers specific for the first nucleic acid template amplification product are the same.

3. The kit of claim 1, wherein the set of primers specific for the first nucleic acid template and the set of primers specific for the first nucleic acid template amplification product are different.

4. The kit of claim 1, wherein at least one of the primers in one of the sets is labeled.

5. The kit of claim 1, wherein the first nucleic acid template and second nucleic acid template are present in equal amounts in the first container.

6. The kit of claim 1, wherein the first nucleic acid template and second nucleic acid template are non-overlapping templates on a single nucleic acid molecule.

7. The kit of claim 1, wherein the first nucleic acid template and second nucleic acid template are overlapping templates on a single nucleic acid molecule.

8. The kit of claim 1, wherein the first nucleic acid template is RNA.

9. The kit of claim 8, wherein the second nucleic acid template is DNA.

10. The kit of claim 1, wherein the first nucleic acid template and second nucleic acid template are the same length or within 10 nucleotides of the same length.

11. The kit of claim 1, wherein the kit comprises an intercalating dye.

12. The kit of claim 1, wherein the kit comprises the first labeled probe specific for an amplification product of the first nucleic acid template.

13. The kit of claim 1, wherein the kit comprises the second labeled probe specific for an amplification product of the second nucleic acid template.

14. The kit of claim 1, wherein the kit comprises the first labeled probe specific for an amplification product of the first nucleic acid template and the second labeled probe specific for an amplification product of the second nucleic acid template.

15. The kit of claim 1, wherein at least one of the primers in the set of primers specific for the second nucleic acid template is labeled.

16. The kit of claim 1, wherein at least one of the primers in the set of primers specific for the first nucleic acid template amplification product is labeled.

* * * * *